United States Patent
Avar et al.

(10) Patent No.: US 6,441,244 B1
(45) Date of Patent: Aug. 27, 2002

(54) BENZOPHENONES AND THE USE THEREOF AS PHOTOINITIATORS

(75) Inventors: Lajos Avar, Biel-Benken; René Bär, Basel; Victor Sanahuja, Therwil, all of (CH)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 09/889,437

(22) PCT Filed: Jan. 11, 2000

(86) PCT No.: PCT/IB00/00024

§ 371 (c)(1),
(2), (4) Date: Jul. 12, 2001

(87) PCT Pub. No.: WO00/41990

PCT Pub. Date: Jul. 20, 2000

(30) Foreign Application Priority Data

Jan. 12, 1999 (CH) .............................................. 0047/99

(51) Int. Cl.⁷ ..................... C07C 49/115; C07C 49/215; C07C 49/76; C07C 45/00; C07C 211/00; C07D 265/30

(52) U.S. Cl. ................ 568/327; 568/328; 568/332; 568/333; 568/334; 568/336; 568/312; 568/314; 568/315; 568/321; 544/106; 544/178; 546/191; 546/195; 546/196; 546/204; 564/316

(58) Field of Search ................................ 568/327, 328, 568/332, 333, 334, 336, 312, 314, 315, 321; 544/106, 178; 546/191, 195, 196, 204; 564/316

(56) References Cited

U.S. PATENT DOCUMENTS

| | | | |
|---|---|---|---|
| 3,898,275 A | * | 8/1975 | Houlihan |
| 3,936,479 A | | 2/1976 | Avar et al. |
| 3,957,885 A | * | 5/1976 | Karrer et al. |
| 4,308,400 A | | 12/1981 | Felder et al. |
| 4,315,807 A | | 2/1982 | Felder et al. |
| 4,318,791 A | | 3/1982 | Felder et al. |
| 4,321,118 A | | 3/1982 | Felder et al. |
| 4,347,111 A | | 8/1982 | Gehlhaus et al. |
| 4,477,681 A | | 10/1984 | Gehlhaus et al. |
| 4,582,862 A | | 4/1986 | Berner et al. |
| 4,721,734 A | | 1/1988 | Gehlhaus et al. |

FOREIGN PATENT DOCUMENTS

| | | |
|---|---|---|
| EP | 0 003 002 | 7/1979 |
| FR | 2 391 183 | 12/1978 |
| FR | 2 627 486 | 11/1989 |
| GB | 2 025 991 | 1/1980 |

OTHER PUBLICATIONS

Chemical Abstract, vol. 114, No. 16, Apr. 22, 1991, Aragones Apodaca, et al., "Manufacture of 1–hydroxycyclohexyl aryl ketones for use as photoinitiators."
International Search Report for Application Serial No. PCT/IB00/00024, mailed Mar. 13, 2000.
International Preliminary Examination Report, for Application Serial No. PCT/IB00/00024, mailed Apr. 9, 2001.
English Abstract of FR 2 627 486; Nov. 2, 1989.

* cited by examiner

Primary Examiner—Johann Richter
Assistant Examiner—Sikarl A. Witherspoon
(74) Attorney, Agent, or Firm—Anthony A. Bisulca

(57) ABSTRACT

The invention relates to new compounds of the formula (I)

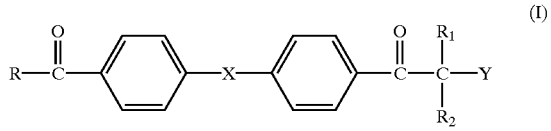

in which
 R is phenyl, $C_{1-4}$alkyl-, $C_{1-4}$alkoxy- or halogen-substituted phenyl, naphthyl or an aromatic ring containing heteroatoms;
 X is O or S;
 $R_1$ and $R_2$ are each a methyl radical or $R_1$ and $R_2$ together are a $C_{4-8}$alkylene radical;
 Y is hydroxyl, $C_{1-12}$alkoxy, $C_{1-4}$alkylamino, di-$C_{1-4}$alkylamino or a piperidine or morpholine ring that is attached by its nitrogen atom;
to a process for preparing them and to their use as photoinitiators and/or photosensitizers.

7 Claims, No Drawings

BENZOPHENONES AND THE USE THEREOF AS PHOTOINITIATORS

The invention relates to new compounds which can be used as photoinitiators and/or photosensitizers, to a process for preparing these compounds and to their use as photoinitiators and/or photosensitizers.

The new compounds are of the general formula (I)

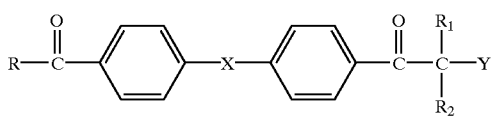

in which
R is phenyl, $C_{1-4}$alkyl-, $C_{1-4}$alkoxy- or halogen-substituted phenyl, naphthyl or an aromatic ring containing heteroatoms;
X is O, S, SO or $SO_2$;
$R_1$ and $R_2$ are each an $C_{1-4}$alkyl radical together having from 4 to 16 carbon atoms or
$R_1$ and $R_2$ together are a $C_{4-8}$alkylene radical;
Y is hydroxyl, $C_{1-12}$alkoxy, $C_{1-4}$alkylamino, di-$C_{1-4}$alkylamino or a piperidine or morpholine ring that is attached by its nitrogen atom.

Preferably, R is an unsubstituted phenyl ring or a chloro- or $C_{1-4}$alkyl-substituted phenyl ring, X is oxygen, $R_1$ and $R_2$ are each a methyl radical and Y is hydroxyl or morpholine.

The compounds of the formula (I) are prepared by halogenating compounds of the formula (II)

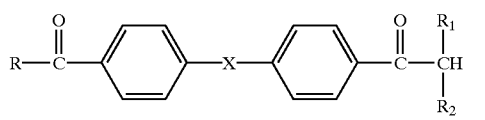

in which R, X, $R_1$ and $R_2$ are as defined above and exchanging the halogen radical for the group Y using corresponding compounds. It is preferred to use elemental bromine and to exchange the bromine radical for hydroxyl, alkoxy or amino in an alkaline medium.

The compounds of the formula (II) are likewise new and may be prepared by reacting compounds of the formula (III)

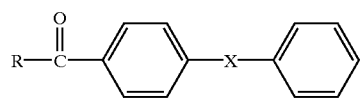

in which R and X are as defined above with compounds of the formula (IV)

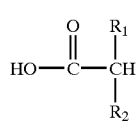

and/or their reactive derivatives, in which $R_1$ and $R_2$ are as defined above, in the presence of appropriate catalysts, e.g. $AlCl_3$.

All process steps are reactions which are known per se, and may be carried out in analogy to processes already described, under known reaction conditions.

The new compounds are photoinitiators and/or photosensitizers for photopolymerizable unsaturated compounds.

Examples of such compounds are unsaturated monomers such as esters of acrylic or methacrylic acid, e.g. methyl, ethyl, n- or tert-butyl, isooctyl or hydroxyethyl acrylate, methyl or ethyl methacrylate, ethylene diacrylate, neopentyl diacrylate, trimethylolpropane triacrylate, pentaerythritol tetraacrylate or pentaerythritol triacrylate; acrylonitrile, methacrylonitrile, acrylamide, methacrylamide, N-substituted (meth)acrylamides; vinyl esters such as, for example, vinyl acetate, propionate, acrylate or succinate; other vinyl compounds such as vinyl ethers, styrene, alkylstyrenes, halostyrenes, divinylbenzene, vinylnaphthalene, N-vinylpyrrolidone, vinyl chloride or vinylidene chloride; allyl compounds such as diallyl phthalate, diallyl maleate, triallyl isocyanurate, triallyl phosphate or ethylene glycol diallyl ether, and the mixtures of such unsaturated monomers.

Further photopolymerizable compounds include unsaturated oligomers or polymers and their mixtures with unsaturated monomers. These include thermoplastic resins containing unsaturated groups such as fumaric ester, allyl groups or acrylate or methacrylate groups. These unsaturated groups are generally attached to the main chain of these linear polymers by way of functional groups. Great importance is possessed by mixtures of oligomers with mono- and polyunsaturated monomers. Examples of such oligomers are unsaturated polyesters, unsaturated acrylic resins and isocyanate- or epoxy-modified acrylate oligomers and also polyether acrylate oligomers. Examples of polyunsaturated compounds include in particular the acrylates of diols and polyols, e.g. hexamethylene diacrylate or pentaerythritol tetraacrylate. As monounsaturated monomers, as well, preference is given to acrylates such as, for example, butyl acrylate, phenyl acrylate, benzyl acrylate, 2-ethylhexyl acrylate or 2-hydroxypropyl acrylate. By selecting from the various representatives of the three components it is possible to vary the consistency of the unpolymerized mixture and also the plasticity of the polymerized resin.

Besides these three-component mixtures, two-component mixtures play a particularly important part in the case of the polyester resins. These two-component mixtures generally consist of an unsaturated polyester and a vinyl compound. The unsaturated polyesters are oligomeric esterification products of at least one unsaturated dicarboxylic acid such as, for example, maleic, fumaric or citraconic acid and generally at least one saturated dicarboxylic acid, such as phthalic acid, succinic acid, sebacic acid or isophthalic acid, for example, with glycols such as ethylene glycol, 1,2-propanediol, diethylene or triethylene glycol or tetramethylene glycol, for example, with monocarboxylic acids and monoalcohols usually being used as well for the purpose of modification. These unsaturated polyesters are commonly dissolved in a vinyl or allyl compound, with styrene being used preferably for this purpose.

Photopolymerizable systems as used for various purposes generally include not only the photopolymerizable compounds and the photoinitiator but also a number of other additions. Thus in many cases it is common to add thermal inhibitors, whose purpose is to protect the systems against premature polymerization, especially during the preparation of the systems by mixing of the components.

In order to increase the dark storage stability it is possible to add copper compounds such as copper naphthenate, stearate or octoate, phosphorus compounds such as triphenylphosphine, tributylphosphine, triethyl phosphite, triphenyl phosphite or tribenzyl phosphate, quaternary ammonium compounds such as tetramethylammonium chloride or trimethylbenzylammonium chloride, or hydroxylamine derivatives such as N-diethylhydroxylamine, for example.

Photopolymerizable systems further include—depending on intended use—fillers such as silica, talc or gypsum, pigments, dyes, fibers, thixotropic agents or leveling assistants.

It is also possible to use combinations with known photoinitiators, such as benzoin ethers, dialkoxyacetophenones or benzil ketals.

For the photopolymerization of thin films and printing inks in particular it is possible to use combinations of the photoinitiator of the invention with amines and/or aromatic ketones. Examples of amines are triethylamine, N-methyldiethanolamine, N-dimethylethanolamine and p-dimethylaminobenzoic esters. Examples of ketones are benzophenone, substituted benzophenone derivatives, Michler's ketone, anthraquinone and anthraquinone derivatives, and also thioxanthone and its derivatives.

Photocuring is of great importance for printing inks, since the drying time of the binder is a critical factor for the production speed of graphic products and should be within the order of fractions of seconds. The initiator of the invention is also highly suitable for photocurable systems for producing printing plates. In this case mixtures, for example, of soluble linear polyamides with photopolymerizable monomers, such as acrylamides, and a photoinitiator are used. Films or plates of these systems are exposed via the negative (or positive) of the print original and the uncured portions are subsequently washed out using a solvent.

A further field of use of UV curing is that of metal coating, an example being the painting of metal sheets for tubes, cans or bottle caps, and also the UV curing of plastics coatings, examples being floor or wall coverings based on PVC.

Examples of the UV curing of paper coatings are the colorless varnishing of labels, record sleeves or book covers.

For the cited fields of application, the photoinitiator is employed appropriately in amounts of from 0.1 to 20% by weight, preferably from about 0.5 to 5% by weight, based on the photopolymerizable or crosslinkable system. By system in this context is meant the mixture of the photopolymerizable or crosslinkable compound, the photoinitiator and the other fillers and additives, as used in the respective application.

The photoinitiator is generally added to the photopolymerizable systems by means of simple stirred incorporation, since the majority of these systems are liquid or readily soluble. Usually, the initiator dissolves, thereby ensuring its uniform distribution and also the transparency of the polymers.

The polymerization takes place in accordance with the known methods of photopolymerization by irradiation with light high in short-wave radiation. Examples of suitable light sources are medium-pressure, high-pressure and low-pressure mercury lamps and also superactinic fluorescent tubes whose emission maxima are situated within the range between 250 and 400 nm.

EXAMPLES a) 13.7 g of p-phenoxybenzophenone

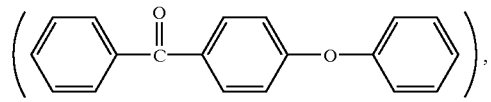

m.p. 69–71° C., are introduced into 100 ml of chlorobenzene together with 6 g of isobutyryl chloride, 15 g of $AlCl_3$ are added in portions to this solution over the course of 8 hours at 8° C., and the mixture is stirred overnight. Following decomposition of the $AlCl_3$ complex with ice-water, the organic phase is separated off and washed with water and the solvent is removed by distillation. The residue is crystallized from isopropanol. White crystals of m.p. 97–99° C.

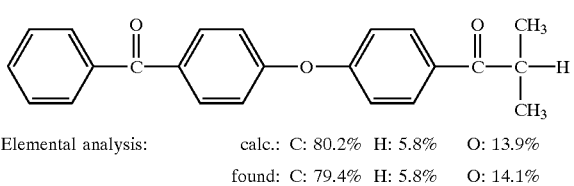

Elemental analysis: calc.: C: 80.2% H: 5.8% O: 13.9%
found: C: 79.4% H: 5.8% O: 14.1% b) 8.6 g of the product from stage a) are introduced into 80 ml of glacial acetic acid, 4.8 9 of bromine are added over the course of 1 hour with stirring at 15° C. and the reddish brown solution is stirred at 30° C. for a further 5 hours. Then the solution is poured into 500 ml of ice-water, and the product precipitates. The precipitate is filtered off with suction, washed with water and crystallized from isopropanol. White crystals of m.p. 131–132° C.

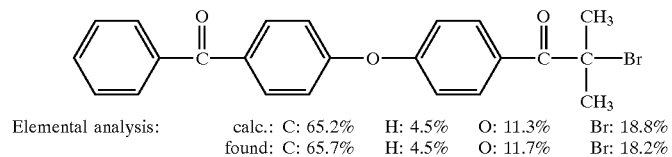

Elemental analysis: calc.: C: 65.2% H: 4.5% O: 11.3% Br: 18.8%
found: C: 65.7% H: 4.5% O: 11.7% Br: 18.2% c) 8.9 g of the product from stage b) are dissolved in 30 ml of isopropanol and heated to 60° C., in the course of which a clear solution is formed. The solution is then admixed dropwise with a solution of 0.88 g of NaOH in 10 ml of water over the course of 3 hours at the same temperature, in the course of which the reaction product precipitates. The precipitate is filtered off with suction at 5° C. and dried. White crystals of m.p. 113–1140C.
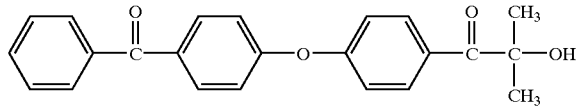
| Elemental analysis: | calc.: C: 76.6% | H: 5.5% | O: 17.7% |
| --- | --- | --- | --- |
| | found: C: 76.9% | H: 5.4% | O: 17.7% |
The method of Example 1 is also used to prepare the following examples of the table:
TABLE
| Example | Formula | Melting Point |
| --- | --- | --- |
| 2a) | | 100.5–101.5° C. |
| 2b) | | 114–115° C. |
| 2c) | | 91–92° C. |
| 3a) | | 97–98° C. |
| 3b) | | 124–125° C. |
| 3c) | | 95–96° C. |
| 4a) | | resin |
| 4b) | | resin |

TABLE-continued

| Example | Formula | Melting Point |
|---|---|---|
| 4c) | 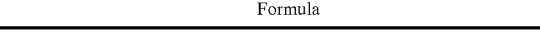 | resin |

Use Example 1

A mixture consisting of 60 g of a prepolymer of the formula:

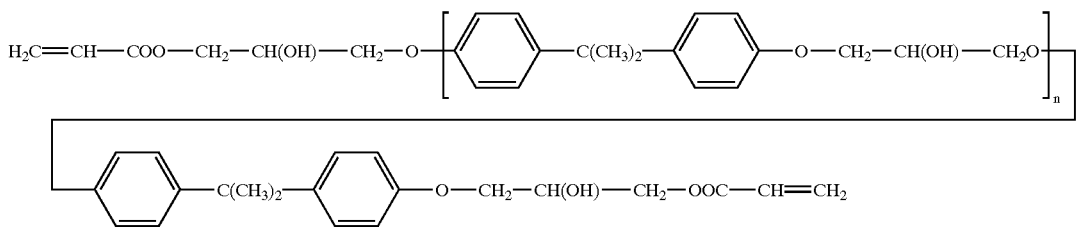

having a viscosity of approximately 9 000 poise (at 77° C.), 35 g of pentaerythritol tetraacrylate and 5 g of the compound

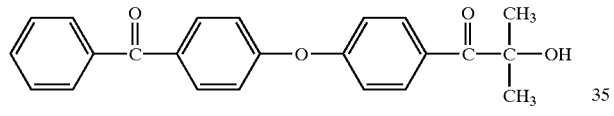

is applied using a spatula to coated art paper in an amount of 3.5 g/m² and is cured in a UV Mini-Cure device at a belt speed of 72 m/min to give a glossy film.

Use Example 2

3 parts of a photoinitiator are blended with 100 parts of an amine-modified polyether acrylate (viscosity at 23° C.: 600 mPas)—Laromer© PO 84F (BASF AG).

A test is carried out to determine the curing rate, as the belt speed with which a liquid coating film, applied to white paper, can be passed under an undoped high-pressure mercury lamp (output: 120 W/cm lamp length; distance of lamp from substrate: 12 cm). to give a coating which adheres and which is resistant to scratching by fingernail. The liquid coating films are applied using a 100 μm spiral-wound coating bar.

Use Example 3 parts of a photoinitiator are blended with a mixture of 90 parts of an amine-modified polyacrylate (viscosity at 23° C.: 600 mPas)—Laromer© PO 84F (BASF AG)—and 10 parts of anatase. A measurement is made of the coat thickness which can be cured right through. For this purpose, the coating material, introduced into a vessel with a depth of about 1 cm, is irradiated at a belt speed of 5 m/min. The cured coat is washed off with ethyl acetate and its thickness is measured.

What is claimed is:

1. Compounds of the general formula (I)

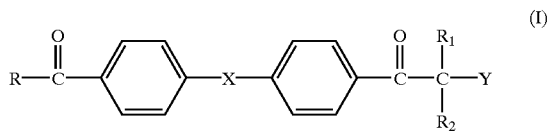

in which

R is phenyl, $C_{1-4}$alkyl-, $C_{1-4}$alkoxy- or halogen-substituted phenyl, naphthyl or an aromatic ring containing heteroatoms;

X is O or S;

$R_1$ and $R_2$ are each a methyl radical or $R_1$ and $R_2$ together are a $C_{4-8}$alkylene radical;

Y is hydroxyl, $C_{1-12}$alkoxy, $C_{1-4}$alkylamino, di-$C_{1-4}$alkylamino or a piperidine or morpholine ring that is attached by its nitrogen atom.

2. Compounds according to claim 1 in which R is an unsubstituted or chloro- or $C_{1-4}$alkyl-substituted phenyl ring, X is oxygen, $R_1$ and $R_2$ are each a methyl radical and Y is hydroxyl or morpholine.

3. Process for preparing compounds of the general formula (I) according to claim 1, characterized in that compounds of the formula (II)

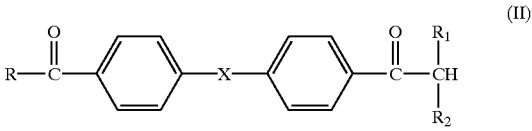

in which R, X, $R_1$ and $R_2$ are as defined in claim 1 for formula (I) are halogenated and the halogen radical is exchanged for the group Y using corresponding compounds.

4. Compounds of the formula (II)

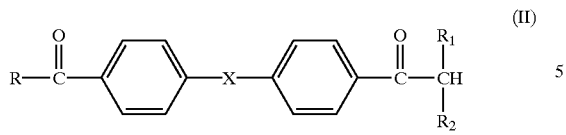

R is phenyl, $C_{1-4}$alkyl-, $C_{1-4}$alkoxy- or halogen-substituted phenyl, naphthyl or an aromatic ring containing heteroatoms;
X is O or S; and
$R_1$ and $R_2$ are each a methyl radical or $R_1$ and $R_2$ together are a $C_{4-8}$alkylene radical.

5. A process for preparing compounds of the formula (II)

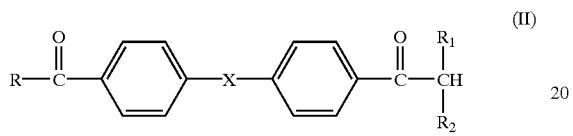

in which
R is phenyl, $C_{1-4}$alkyl-, $C_{1-4}$alkoxy- or halogen-substituted phenyl, naphthyl or an aromatic ring containing heteroatoms;
X is O or S; and
$R_1$ and $R_2$ are each a methyl radical or $R_1$ and $R_2$ together are a $C_{4-8}$alkylene radical comprising the step of reacting compounds of the formula (III)

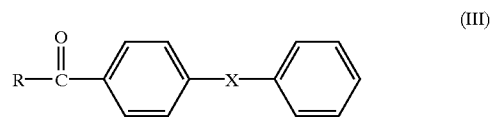

in which R and X are as defined above, with compounds of the formula (IV)

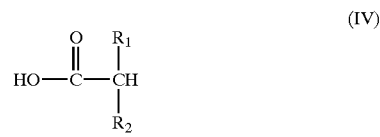

and/or their reactive derivatives, in which $R_1$ and $R_2$ are as defined above, in the presence of appropriate catalysts.

6. A photoinitiator for phatopolymerizable unsaturated compounds comprising a compound of the formula (I) according to claim 1.

7. A photosensitizer for photopolymerizable unsaturated compounds comprising a compound of the formula (I) according to claim 1.

* * * * *